United States Patent
Maruyama et al.

[11] Patent Number: 5,967,993
[45] Date of Patent: *Oct. 19, 1999

[54] VITAL INFORMATION PROCESSING APPARATUS

[75] Inventors: Mitsuya Maruyama; Toshihiko Yamagata; Tamon Mizoguchi, all of Tokyo, Japan

[73] Assignee: Fukuda Denshi Kabushiki Kaisha, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/903,856

[22] Filed: Jul. 31, 1997

[30] Foreign Application Priority Data

Aug. 1, 1996 [JP] Japan ................................. 8-203496

[51] Int. Cl.$^6$ ........................................... A61B 5/04

[52] U.S. Cl. ............................................ 600/509; 128/901

[58] Field of Search ................................. 600/509, 508, 600/513, 493, 481, 500, 502; 128/901

[56] References Cited

U.S. PATENT DOCUMENTS

| | | | |
|---|---|---|---|
| 4,617,937 | 10/1986 | Peel et al. | 600/493 |
| 4,770,184 | 9/1988 | Greene, Jr. et al. | 600/454 |
| 5,119,822 | 6/1992 | Niwa | 600/485 |
| 5,355,890 | 10/1994 | Aguirre et al. | 600/493 |

*Primary Examiner*—William E. Kamm
*Assistant Examiner*—George R. Evanisko
*Attorney, Agent, or Firm*—Merchant & Gould P.C.

[57] ABSTRACT

There is provided a vital information processing apparatus capable of effectively reducing small-amplitude noise and isolated noise without degrading an abrupt change portion in a processing target vital signal. A vital signal detected by a vital signal detector (10) is input from a vital signal input unit (20). A sync signal extractor (25) extracts, e.g., the QRS wave form of an electrocardiogram signal of the input signal and outputs the extracted wave as a sync signal (26). A preprocessor (30) performs predetermined preprocessing for the processing target vital signal, e.g., a K sound signal and outputs the preprocessed signal to median filters (40, 45). Each of the median filters (40, 45) filters the Korotkoff sounds using the QRS signal (26) as the index value and outputs the resultant signal.

8 Claims, 2 Drawing Sheets

VITAL INFORMATION PROCESSING APPARATUS

BACKGROUND OF THE INVENTION

The present invention relates to a vital information processing apparatus capable of effectively reducing noise components contained in vital information and, more particularly, to a vital information processing apparatus which can extract each vital signal representing an electrocardiogram, blood pressure, pulse wave, respiration, EEG (electroencephalogram), or the like and has, as a processing target, Korotkoff sounds, blood pressure, electrocardiogram, respiration, an image data signal representing MRI, CT, radioisotope, or the like.

In a vital information processing apparatus for detecting and processing a vital signal, a vital signal to be detected is generally a signal having a very low level and contains a large number of noise components. For this reason, demand has conventionally arisen for effectively reducing the noise components contained in the vital signal prior to processing of vital information.

To reduce the noise components, the following conventional methods are used. The reference waveform of a vital signal is compared with the waveform of a detected signal to extract only signals having high similarity degrees. Alternatively, the feature points of a signal are extracted to detect the generation period of the signal in accordance with the generation period of the feature points, and signal components falling outside the generation period of the signal are eliminated.

In the method of extracting signals having high similarity degrees, all the signals to be processed must be precisely compared with the reference waveform. That is, to make an accurate judgment, a very large volume of information must be processed. This method cannot be used when vital signals are processed in real time. When vital signals are to be forcibly processed in real time, the processing speed of an apparatus must be increased. The apparatus becomes inevitably bulky and expensive as a whole.

In the method of detecting the generation period of the signal and eliminating signals falling outside this generation period, a filter for passing only signals in a signal band using the signal periodicity is arranged, and a signal having a desired frequency is defined as an effective signal using this filter. According to this method, however, a noise signal whose frequency is greatly shifted from the frequency band can be reduced, but a noise component present in the same frequency band as that of the effective signal cannot be reduced.

SUMMARY OF THE INVENTION

The present invention has been made to solve the conventional problems described above, and has as its object to provide a vital information processing apparatus capable of effectively reducing noise components contained in a vital signal detected.

The present invention has been made to solve the conventional problems described above, and has as its object to solve the above problems and provide a vital information processing apparatus which is capable of effectively reducing noise components contained in a vital detection signal and has the following arrangement.

That is, a vital information processing apparatus comprises vital signal input means for inputting a vital signal, sync signal extraction means for extracting a sync signal from a predetermined vital signal in the vital signal input by the vital signal input means, and a median filter for filtering the vital signal as a processing target which is contained in the input vital signal and indexed by the sync signal extracted by the sync signal extraction means, thereby outputting a median value.

The predetermined vital signal in the vital signal input by the vital signal input means is made identical to the vital signal serving as the processing target. Alternatively, the sync signal extraction means generates a sync signal from an electrocardiogram signal and defines the vital signal, i.e., the processing target as a Korotkoff sound signal.

For example, the median filter performs processing of a median filter y having a rank K (K is a positive integer of 0 or more) for a processing target signal x position-indexed by a sync signal s. Letting x(n), s(m), and y(n) be the signal x at a point n, the position index of the mth sync signal s, and the output from the median (center value of (2K+1) processing target signal values: (K+1)th largest signal value) filter having the rank K, respectively, the following relation is obtained.

$$y(n)[n<s(J)] \text{ is indefinite } y(n)=y\{s(m)+i\}=\text{median}[x\{s(m-K)+i\},\ldots,x(n),\ldots,x\{s(m+K)+i\}] \ m=J, J+1, J+2, \ldots J=0, 1, 2, 3, \ldots i=0, 1, 2, \ldots, s(m+1)-s(m)-1 \quad (1)$$

In addition, the median filter is an order statistic filter. Alternatively, the median filter is a weighted median filter.

Other features and advantages of the present invention will be apparent from the following description taken in conjunction with the accompanying drawings, in which like reference characters designate the same or similar parts throughout the figures thereof.

DETAILED DESCRIPTION OF THE PREFERRED EMBODIMENTS

The preferred embodiments of the present invention will be described in detail below with reference to the accompanying drawings.

First Embodiment

Figure 1:
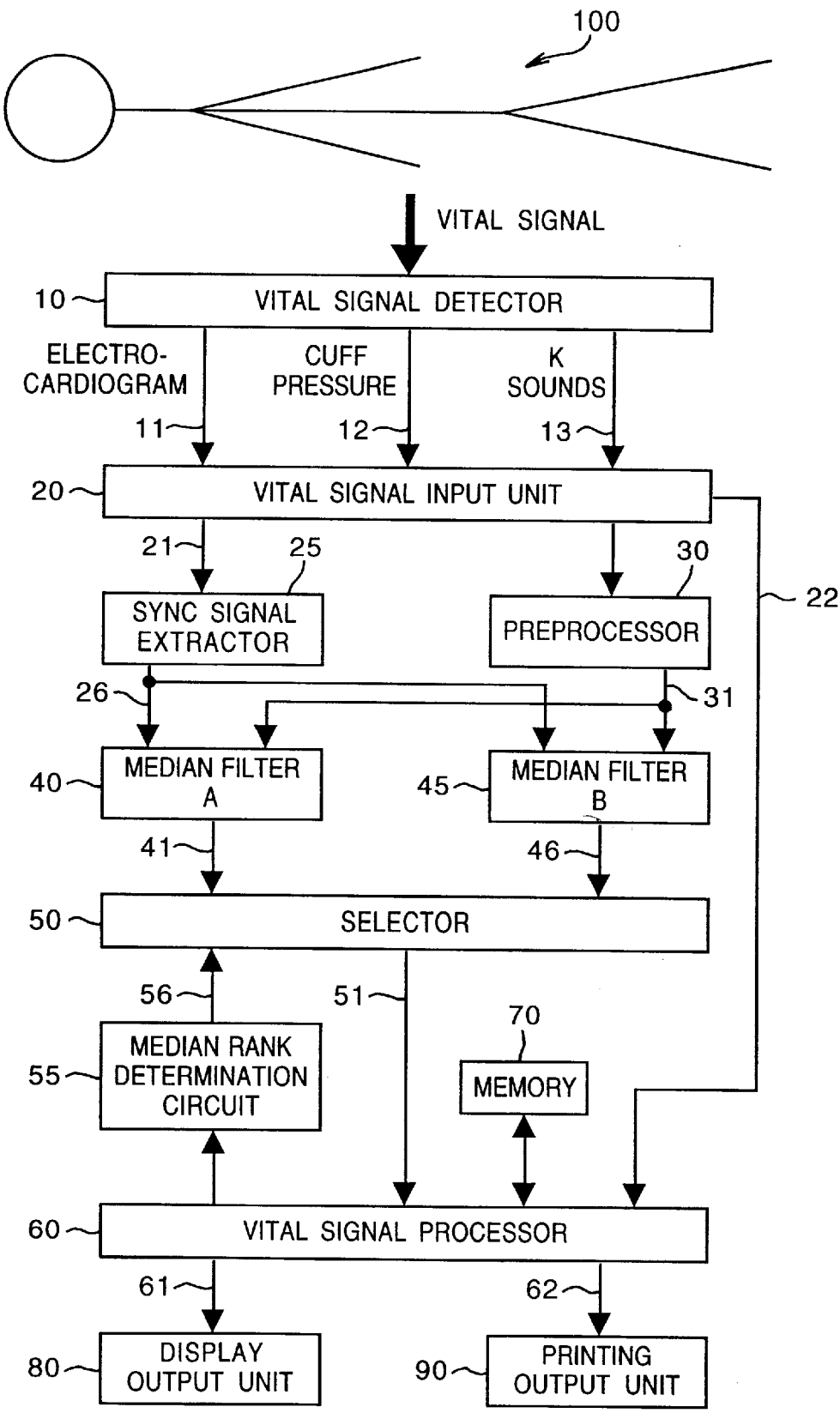
FIG. 1 is a block diagram showing the arrangement of a vital information processing apparatus according to an embodiment of the present invention.

FIG. 1 is a block diagram showing the arrangement of a vital information processing apparatus according to an embodiment of the present invention. Referring to FIG. 1, reference numeral 10 denotes a vital signal detector for detecting a vital signal from a living body 100 as a patient to be examined. In this embodiment, an electrocardiogram signal 11 for detecting electrocardiogram information, a cuff pressure signal 12 for measuring a blood pressure, and a K (Korotkoff) sound signal 13 for detecting K sounds from a microphone or the like can be detected as vital signals.

Vital signals to be detected are not limited to the ones described above. Various vital signals can be detected by changing detection elements. For example, an EEG signal for detecting an EEG, a respiration signal for detecting respiration, image data signals (e.g., MRI, CT, and radioisotope), and the like can be detected.

Reference numeral 20 denotes a vital signal input unit for inputting each vital signal detected by the vital signal detector 10. The vital signal input unit 20 selects a desired one of the input vital signals to a sync signal extractor 25 and a preprocessor 30. If noise reduction processing to be described in detail later is not required, the desired vital signal is directly input to a vital signal processor 60.

The sync signal extractor 25 extracts a sync signal from the selected vital signal from the vital signal input unit 20. The preprocessor 30 performs preprocessing for a selected signal as a processing target from the vital signal input unit 20 as in the conventional case (e.g., filtering processing for frequency components except the necessary band, pre-noise reduction processing, and envelope generation processing). In this embodiment, a signal pass band can be manually adjusted.

Reference numerals 40 and 45 denote median (center value) filters for performing median filter processing for a processing target signal 31 from the preprocessor 30 with a rank n (n is an integer of 0 or more) in accordance with a sync signal 26 extracted by the sync signal extractor 25. More specifically, in this embodiment, each median filter comprises a nonlinear filter for outputting a median (center value: (K+1)th largest signal value) of the consecutive (2K+1) processing target signal values as follows:

$$y(n)=\text{median}[x(n-k), \ldots, x(n), \ldots, x(n+K)] \quad (2)$$

Reference numeral 50 denotes a selector for selecting one of the median filters A 40 and B 45 in accordance with a selection signal 56 from a median rank determination circuit 55 and outputs a signal representing the selected median filter to the vital signal processor 60. The median rank determination circuit 55 determines the rank n of the median filter and outputs the selection signal 56 so as to cause the selector 50 to select the median filter and output a signal representing the selected median filter.

The vital signal processor 60 performs predetermined processing for the selection signal 51 from the selector 50. The vital signal processor 60 checks the quality of this input signal and instructs the rank n of the median filter to be selected to the median rank determination circuit 55 in accordance with the check result. A memory 70 stores the processing results. A display output unit 80 displays and outputs the processing results. A printing output unit 90 prints and outputs the processing results.

In the embodiment having the above arrangement, a vital signal detected by the vital signal detector 10 is received by the vital signal input unit 20. The vital signal input unit 20 outputs a signal subjected to noise reduction to the preprocessor 30 and a vital signal used as a sync signal (the center value for the median filter to be described later) to the sync signal extractor 25. Each median filter 40 or 45 performs median filtering of the processing target vital signal from the preprocessor 30 by using the sync signal from the sync signal extractor 25 as an index.

The selector 50 selects the median filter having the median rank determined by the median rank determination circuit 55 and outputs a signal representing the selected median filter to the vital signal processor 60. The noise component is properly reduced from the processing target signal by filtering using the median filter. Highly reliable vital signal processing can be performed for this processing target signal.

The vital signal processor 60 stores the processing result in the memory 70, displays and outputs the processing result on the display output unit 80, or prints and outputs the processing result at the printing output unit 90, as needed.

In this embodiment, as the sync signal to be used in the median filters 40 and 45, an electrocardiogram, blood pressure, pulse wave, respiration, or EEG signal, or the like can be extracted. As a vital signal serving as a processing target, Korotkoff sounds (K sounds), blood pressure, electrocardiogram, respiration, an image data signal of MRI, CT, radioisotope, or the like can be used. In noise reduction processing to be described later, median filter processing having the rank n (n is a positive integer of 0 or more) is performed for a processing target signal indexed by the sync signal.

For the descriptive simplicity, in the following description, blood pressure measurement is exemplified in which electrocardiogram information is used as a sync signal, and the processing target is blood pressure measurement processing. This combination can be performed for all the choices described above. The basic filter arrangement is kept unchanged for all the combinations.

For example, in blood pressure measurement in which electrocardiogram information is used as the sync signal, the vital signal detector 10 is arranged to include a vital electrode attached to a predetermined measurement portion of the living body 100, thereby detecting electrocardiogram information through this vital electrode. The vital signal input unit 20 amplifies this electrocardiogram information to a detection signal having a predetermined level, performs necessary baseline processing, and outputs the processed signal to the sync signal extractor 25. For example, when the input signal represents electrocardiogram information, the sync signal extractor 25 detects a QRS waveform from the input signal and outputs the QRS wave detection signal to the median filters A 40 and B 45 as the sync signal 26.

In blood pressure measurement, to detect a vascular sound and measure the highest and lowest blood pressures by pressing the blood vessel at the blood pressure measurement portion with a cuff (not shown), the vital signal detector 10 is arranged to include a microphone for collecting the vascular sound. A detection signal from the microphone is output to the vital signal input unit 20. The vital signal input unit 20 converts this signal into a signal having a predetermined level and outputs it as a K sound signal. Upon reception of the K sound signal, the preprocessor 30 performs preprocessing such as elimination of signals having frequencies higher and lower than that of the K sounds by a bandpass filter for passing only the frequency band including the K sound signal, envelope processing representing an amplitude component, and the like. The preprocessor 30 outputs the preprocessed signal to the median filters A 40 and B 45 as the K sound signal 31.

Note that the vital signal input unit 20 directly outputs, to the vital signal processor 60, a signal (22) having a low necessity for special signal processing, e.g., a cuff pressure detection result in blood pressure measurement.

The median filters A 40 and B 45 calculate the medians of the input signals, extract the data of the respective points for time-series data in units of set ranks, and perform median filtering, thereby reducing spike noise components and the like.

Whether the vital signal processor 60 selects the output from the median filter A 40 or B 45 may be determined by a manual operation of the operator upon checking the display of the selection result on the display output unit 80 or by automatically specifying an optimal median filter upon comparison between the outputs in the vital signal processor 60.

Note that the two median filters A 40 and B 45 are illustrated in FIG. 1, but the number of median filters is not limited to a specific one, and the median rank may be arbitrary changed within the arbitrary integer range of 0 or more.

A median filter used in this embodiment will be described in detail below.

The median filter of this embodiment performs processing of a median filter y having a rank K (K is a positive integer of 0 or more) for a processing target signal x position-indexed by a sync signal s. Letting x(n), s(m), and y(n) be the signal x at a point n, the position index of the mth sync signal s, and the output from the median (center value of (2K+1) processing target signal values: (K+1)th largest signal value) filter having the rank K, respectively, the following relation is obtained.

$$y(n)[n<s(J)] \text{ is indefinite } y(n)=y\{s(m)+i\}=\text{median}[x\{s(m-K)+i\}, \ldots, x(n), \ldots, x\{s(m+K)+i\}] \; m=J, J+1, J+2, \ldots J=0, 1, 2, 3, \ldots \; i=0, 1, 2, \ldots, s(m+1)-s(m)-1 \quad (3)$$

For example, for K=1, $$y(n)[n < s(1)] \text{ is indefinite} \quad (4)$$
$$y\{s(1) + 0\} = \text{median}[x\{s(0) + 0\}, x\{s(1) + 0\}, x\{s(2) + 0\}]$$
$$y\{s(1) + 1\} = \text{median}[x\{s(0) + 1\}, x\{s(1) + 1\}, x\{s(2) + 1\}]$$
$$y\{s(1) + 2\} = \text{median}[x\{s(0) + 2\}, x\{s(1) + 2\}, x\{s(2) + 2\}]$$
$$\vdots$$
$$y\{s(2) + 0\} = \text{median}[x\{s(1) + 0\}, x\{s(2) + 0\}, x\{s(3) + 0\}]$$
$$y\{s(2) + 1\} = \text{median}[x\{s(1) + 1\}, x\{s(2) + 1\}, x\{s(3) + 1\}]$$
$$y\{s(2) + 2\} = \text{median}[x\{s(1) + 2\}, x\{s(2) + 2\}, x\{s(3) + 2\}]$$
$$\vdots$$
$$y(n) = y\{s(m) + i\} = \text{median}[x\{s(m-1) + i\}, x\{s(m) + i\}, x\{s(m+1) + i\}]$$

where i takes a value ranging from 0 to s(m+1)−s(m)−1 (when i=s(m+1)−s(m), then a sync point shifts to the next point, and n=s(m)+i is updated to n=s(m+1)+i).

By using the median filter as the nonlinear filter, small-amplitude noise and isolated noise can be reduced without degrading the signal portion of the processing target. For this reason, when noise is reduced from the Korotkoff sound (K sound) signal by using this filter, the isolated noise can be almost perfectly reduced, thereby obtaining an excellent noise reduction effect.

Figure 2:
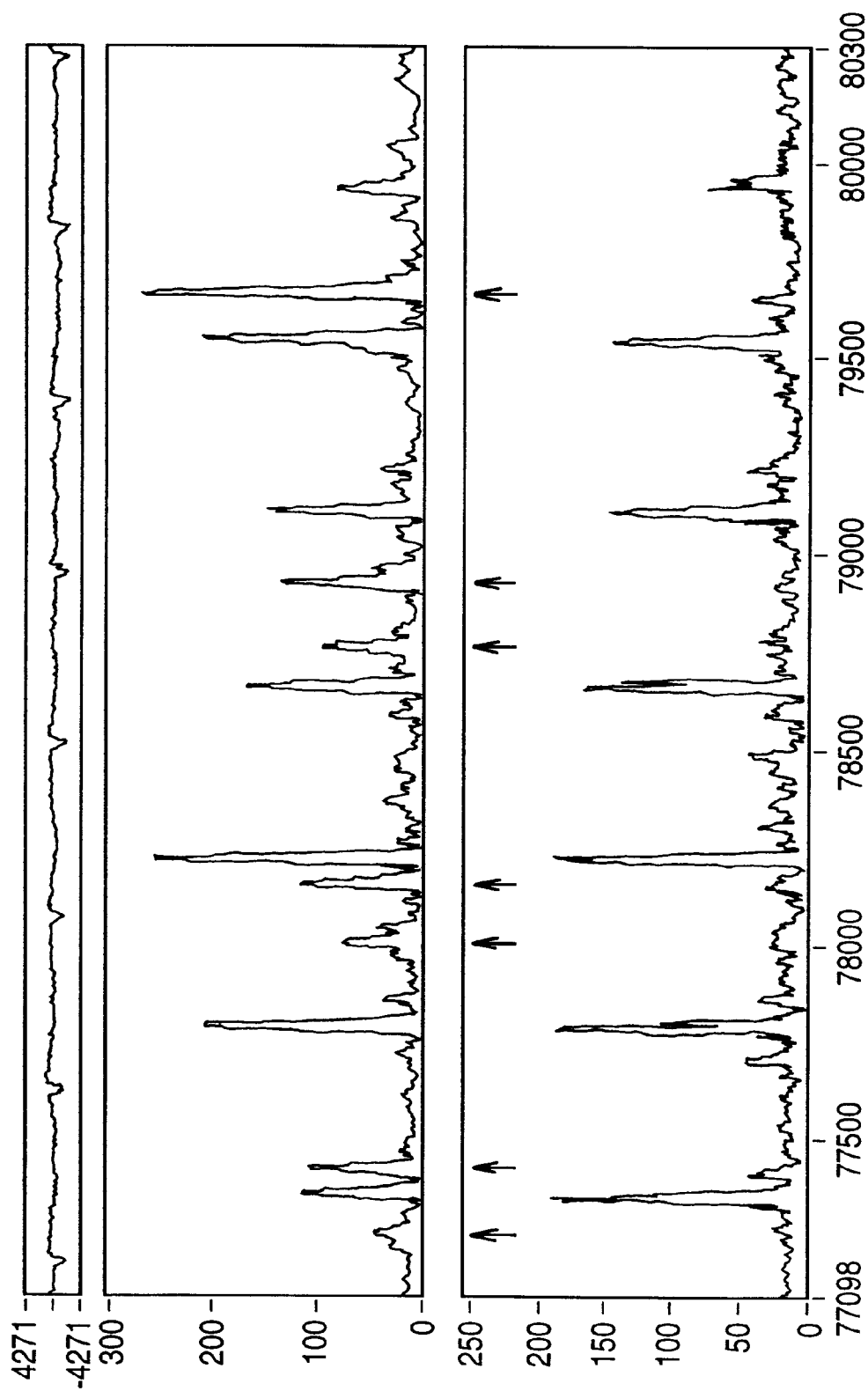
FIG. 2 is a view for explaining the processing result of a vital signal in the embodiment of the present invention.

In this embodiment, the plurality of median filters 40 and 45 having different median ranks K are arranged. For example, the median filters A 40 and B 45 in FIG. 1 are median filters having ranks K of 3 and 5, respectively. The filtering result using the median filter is shown in FIG. 2. In the graph of FIG. 2, the upper one of the three waveforms represents an electrocardiogram waveform serving as a sync signal to the sync signal extractor 25. The middle waveform is an output processing target waveform (median filter input waveform) from the preprocessor 30.

The lower waveform is a median filter output waveform. Isolated noise components indicated by arrows in the middle waveform are almost perfectly reduced, and the processing target waveform rarely deforms, thereby obtaining excellent noise reduction performance.

As described above, according to this embodiment of the present invention, since the median filters are used to reduce the noise components of a vital signal to be processed, a vital information processing apparatus capable of effectively reducing small-amplitude noise and isolated noise can be provided without degrading an abrupt change signal portion. In this case, since another detection vital signal is used as a sync signal, an excellent noise reduction effect can be obtained with a simple arrangement.

In particular, the QRS waveform of the electrocardiogram information is used as a sync signal to obtain a reliable, excellent sync signal. Therefore, the noise components contained in the K sounds can be reliably and accurately reduced.

Second Embodiment

In the above description, the normal median filters are constituted by nonlinear filters represented by equation (1). The present invention, however, is not limited to the above embodiment. A median filter may be any filter based on a similar relationship between the magnitudes of the signal values. Examples of the median filter are a min-filter for outputting the minimum value of the (2K+1) processing target signal values, a mid-range-filter for outputting the average value of the maximum and minimum values, or as a general form, an order statistic filter for rearranging the (2K+1) signals in the ascending order of magnitudes and outputting its linear sum.

The following order statistic filter is used for the median filter 40 or 45 in FIG. 1 in the second embodiment.

An output y(n) of this order statistic filter is defined as follows:

$$y(n) = \sum_{k=-K}^{K} a[\gamma\{x(n-k)\}]x(n-k) \quad (5)$$

The coefficient for x(n−k)−K≦k≦K in this filter is controlled by the rank γ{x(n−k)} (the rearranged ascending order of magnitudes of the signals) of x(n−k) in the signal in the filter window.

Even if a vital signal is processed using the above order statistic filter, the isolated noise can be efficiently reduced, and at the same time degradation of an effective processing target signal can be minimized.

Third Embodiment

The above description exemplifies processing of a vital signal using the normal median filters and the order statistic filters. The present invention, however, is not limited to the above embodiments. Other median filters may be used.

The third embodiment using a weighted median filter for weighting a processing target signal in place of the above median filter will be described below. In the third embodiment, a weighted median filter is used in place of the median filter shown in FIG. 1.

The weighted median filter used in the third embodiment outputs the following signal:

$$y(n) = \text{median}[W(n-K) \odot x(n-K), \ldots, \quad (6)$$
$$W(n) \odot x(n), \ldots, W(n+K) \odot x(N+K)]$$

where ⊙ represents repetition, n⊙x represents repetition of x by n times (i.e., n⊙x=x, . . . , x).

Even if a vital signal is processed using the above weighted median filter, the isolated noise can be efficiently reduced, and at the same time degradation of an effective processing target signal can be minimized.

This weighted median filter is described in detail in, e.g., IEEE transactions on signal processing, VOL. 43, NO. 3, MARCH 1995 "Optimal Weighted Median Filtering Under Structural Constrains".

In the above description, in each embodiment, a signal to be processed is detected from the living body by the vital signal detector 10 and is input from the vital signal input unit 20. The present invention, however, is not limited to the above embodiments. If an input signal is an electrocardiogram signal, the electrocardiogram signal may be directly received in the form of a signal from another processor or as processible data. For example, a signal read by a Holter monitor may be read by and input from the vital signal input unit 20. In this case, the input signal is a vital signal itself, and the input means for the vital signal can input various vital signals including the processing vital signals from various vital signal processors.

The operation can be performed even if a processing target signal is identical to a sync signal. The above operation and effect can be attained regardless of the types of input signals.

According to the present invention, as has been described above, there can be provided a vital information processing apparatus in which a processing target vital signal is filtered using median filters, and small-amplitude noise and isolated noise can be effectively reduced without degrading an abrupt change portion in the processing target vital signal. In this case, a detected vital signal is used as a sync signal to obtain an excellent noise reduction effect with a simple arrangement.

In particular, Korotkoff sounds are processed using an electrocardiogram signal as a sync signal to obtain a reliable and excellent sync signal. Therefore, the noise components contained in the Korotkoff sounds can be reliably and accurately reduced.

In addition, the median filter is replaced with an order statistic filter to allow effective reduction of small-amplitude noise and isolated noise of the processing target vital signal. Alternatively, the median filter is replaced with a weighted median filter to reliably allow effective reduction of small-amplitude noise and isolated noise of the processing target vital signal.

As many apparently widely different embodiments of the present invention can be made without departing from the spirit and scope thereof, it is to be understood that the invention is not limited to the specific embodiments thereof except as defined in the appended claims.

What is claimed is:

1. A vital information processing apparatus comprising:
   vital signal input means for inputting at least one vital signal;
   sync signal generation means for generating a sync signal, s, from a predetermined vital signal inputted by said vital signal input means;
   a median filter;
   selection means for selecting a processing target signal, from the at least one vital signal, for processing the median filter; and
   vital signal index means for indexing the processing target signal using the sync signal, s;
   wherein the median filter filters the processing target signal using the sync signal as an index to output a center value of the processing target signal inputted by the vital signal input means.

2. The apparatus according to claim 1, wherein the predetermined vital signal inputted by said vital signal input means serves as the processing target signal.

3. The apparatus according to claim 1, wherein the predetermined vital signal is an electrocardiogram signals; and the processing target signal is a Korotkoff sound signal.

4. The apparatus according to claim 1, wherein said median filter performs processing of a median filter y having a rank K (K is a positive integer of not less than 0) for the processing target signal x position-indexed by the sync signal s, and an output y(n) from the median (center value of (2K+1) processing target signal values: (K+1)th largest signal value) filter having the rank K is defined as follows:

y(n) [n<s(J)] is indefinite y(n)=y{s(m)+i}=median [x{s(m−K)+i}, . . . , x(n), . . . ,x{s(m+K)+i}]

m=J, J+1, J+2, . . .

J=0, 1, 2, 3, . . .

i=0, 1, 2, . . . , s(m+1)−s(m)−1 where x(n), and s(m) are the processing target signal x at a point n and a position index of the mth sync signal s, respectively.

5. The apparatus according to claim 1, wherein said median filter comprises an order statistic filter.

6. The apparatus according to claim 5, wherein said order statistic filter is defined as follows:

$$y(n) = \sum_{k=-K}^{K} a[\gamma\{x(n-k)\}]x(n-k)$$

7. The apparatus according to claim 1, wherein said median filter comprises a weighted median filter.

8. The apparatus according to claim 7, wherein said weighted median filter is defined as follows:

$$y(n) = \text{median}[W(n-K) \copyright x(n-K), \ldots,$$

$$W(n) \copyright x(n), \ldots, W(n+K) \copyright x(N+K)]$$

* * * * *